(12) United States Patent
Lee et al.

(10) Patent No.: US 9,844,560 B2
(45) Date of Patent: *Dec. 19, 2017

(54) USE OF GINSENOSIDE M1 FOR TREATING LUPUS NEPHRITIS

(71) Applicant: Sheau-Long Lee, Taoyuan (TW)

(72) Inventors: Sheau-Long Lee, Taoyuan (TW); Yu-Chieh Lee, Taoyuan (TW); Ann Chen, Taipei (TW); Kuo-Feng Hua, I-Lan (TW); Shuk-Man Ka, Taipei (TW)

(73) Assignee: Sheau-Long Lee, Taoyuan (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/308,069

(22) PCT Filed: May 4, 2015

(86) PCT No.: PCT/CN2015/078187
§ 371 (c)(1),
(2) Date: Oct. 31, 2016

(87) PCT Pub. No.: WO2015/165422
PCT Pub. Date: Nov. 5, 2015

(65) Prior Publication Data
US 2017/0049792 A1    Feb. 23, 2017

Related U.S. Application Data (60) Provisional application No. 61/987,631, filed on May 2, 2014.

(51) Int. Cl.
*A61K 31/704* (2006.01)
*A61K 45/06* (2006.01)

(52) U.S. Cl.
CPC ............ *A61K 31/704* (2013.01); *A61K 45/06* (2013.01)

(58) Field of Classification Search
None
See application file for complete search history.

(56) References Cited

U.S. PATENT DOCUMENTS 8,080,568 B1 *  12/2011  Kim ................... C07D 471/04
                                                    514/357
8,673,851 B2 *   3/2014  Rastaldi ............. A61K 31/165
                                                    424/198.1

* cited by examiner

*Primary Examiner* — Traviss C McIntosh, III
(74) *Attorney, Agent, or Firm* — WPAT, P.C., Intellectual Property Attorneys; Anthony King (57) ABSTRACT

The present invention provides a method of treating a subject afflicted with lupus nephritis comprising administering to the subject an amount of ginsenoside M1 effective to treat the subject.

5 Claims, 10 Drawing Sheets

Fig. 7 ns
USE OF GINSENOSIDE M1 FOR TREATING LUPUS NEPHRITIS

FIELD OF THE INVENTION

The present invention relates to a new use of ginsenoside M1 for treating lupus nephritis.

BACKGROUND OF THE INVENTION

Lupus nephritis occurs in a sub-population of patient with systemic lupus erythematosus (SLE) and is one of the most severe complications of SLE, associated with significant morbidity and mortality. Systemic lupus erythematosus (SLE) is an autoimmune disorder involving multiple organs injury due to autoantibody production and abnormal cell immunity. The cumulative risks of end stage renal failure were particularly high in patients with severe lupus nephritis, the histopathology of which comprises distinct patterns of injury that were initially defined by the World Health Organization Classification of 1982 as category III, category IV, and categories Vc and Vd. The exact mechanisms for the development or the progression of lupus nephritis remain unclear. There is no definitive treatment for lupus nephritis. Current therapies for lupus nephritis are various combinations of corticosteroids with other cytotoxic agents or immunomodulators, but many of these have various side effects.

Ginsenosides, the main active ingredients of *ginseng*, are known to have a variety of pharmacological activities, e.g. antitumor, antidiabetic, antifatique, antiallergic and antioxidant activities. Ginsenosides share a basic structure, composed of gonane steroid nucleus having 17 carbon atoms arranged in four rings. Ginsenosides are metalized in the body, and a number of recent studies suggest that ginsenoside metabolites, rather than naturally occurring ginsenosides, are readily absorbed in the body and act as the active components. Among them, ginsenoside M1 is known as one metabolite of protopanaxadiol-type ginsenosides via the gypenoside pathway by human gut bacteria. Until now, no prior art references report the effect of ginsenoside M1 in treatment of lupus nephritis.

BRIEF SUMMARY OF THE INVENTION

In the present invention, it is unexpected found that ginsenoside M1 is effective in alleviating the symptoms of lupus nephritis. Therefore, the present invention provides a new approach for treatment of lupus nephritis in a subject.

In particular, the present invention provides a method for treating a subject in need of treatment for lupus nephritis comprising administering a therapeutically effective amount of ginsenoside M1 to the subject.

Specifically, the method of the present invention is effective in reducing one or more symptoms of lupus nephritis in the subject, selected from the group consisting of (1) in the glomerulus: intrinsic cell proliferation, crescents, neutrophil infiltration and fibrinoid necrosis; and (2) in the tubulointerstitial compartment: interstitial (especially peri-glomerular) mononuclear leukocyte inflammation and tubular atrophy with proteinaceous casts. Also, the method of the present invention is effective in reducing proteinuria or hematuria or lowering serum urea nitrogen level or serum creatinine level in the subject.

In some embodiments, ginsenoside M1 is administered in combination with one or more therapeutic agents for treating lupus nephritis known in the art, including but not limited to corticosteroids (such as prednisolone), non-steriodal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors).

Also provided is use of ginsenoside M1 for manufacturing a medicament for treating lupus nephritis.

The details of one or more embodiments of the invention are set forth in the description below. Other features or advantages of the present invention will be apparent from the following detailed description of several embodiments, and also from the appending claims.

BRIEF DESCRIPTION OF THE DRAWINGS

For the purpose of illustrating the invention, there are shown in the drawings embodiments. It should be understood, however, that the invention is not limited to the preferred embodiments shown. In the drawings.

DETAILED DESCRIPTION OF THE INVENTION

Unless defined otherwise, all technical and scientific terms used herein have the meaning commonly understood by a person skilled in the art to which this invention belongs. As used herein, the following terms have the meanings ascribed to them unless specified otherwise.

The articles "a" and "an" are used herein to refer to one or more than one (i.e., at least one) of the grammatical object of the article. By way of example, "an element" means one element or more than one element.

In the present invention, it is unexpectedly found that ginsenoside M1 can prevent development of lupus nephritis by administering it to NZB/W F1 lupus-prone mice. In particular, it is found that animals with lupus nephritis present various symptoms including (1) in the glomerulus: intrinsic cell proliferation, crescents, neutrophil infiltration and fibrinoid necrosis; or (2) in the tubulointerstitial compartment: interstitial (especially peri-glomerular) mononuclear leukocyte inflammation and tubular atrophy with proteinaceous casts, or proteinuria or hematuria, or elevated serum urea nitrogen level or serum creatinine level. The method of the invention is effective in improving any one of these symptoms in patients with lupus nephritis by administering ginsenoside M1.

Ginsenoside M1, 20-O-β-D-glucopyranosyl-20(S)-protopanaxadiol, is one of saponin metabolites known in the art. The chemical structure of ginsenoside M1 is as follows:

Ginsenoside M1 is known as one metabolite of protopanaxadiol-type ginsenosides via the gypenoside pathway by human gut bacteria. Ginsenoside M1 can be found in blood or urine after intake. Ginsenoside M may be prepared from *ginseng* plants through fungi fermentation by methods known in the art, such as Taiwan Patent Application No. 094116005 (1280982) and U.S. Pat. No. 7,932,057, the entire content of which is incorporated herein by reference. In certain embodiments, the *ginseng* plants for preparing the ginsenoside M1 include Araliaceae family, *Panax* genus, e.g. *P. ginseng* and *P. pseudo-ginseng* (also named Sanqi). In general, the method of preparation of ginsenoside M1 includes the steps of (a) providing powder of *ginseng* plant materials (e.g. leaves or stems); (b) providing a fungus for fermenting the *ginseng* plant materials, wherein the fermentation temperature is ranged from 20-50° C., the fermentation humidity is ranged from 70-100%, the pH value is ranged from 4.0-6.0, and the fermentation period is ranged from 5-15 days; (c) extracting and collecting the fermentation products; and (d) isolating 20-O-β-D-glucopyranosyl-20(S)-protopanaxadiol from the fermentation products.

When ginsenoside M1 is described as "isolated" or "purified" in the present invention, it should be understood as not absolutely isolated or purified, but relatively isolated or purified. For example, purified ginsenoside M1 refers to one that is more purified compared to its naturally existing form. In one embodiment, a preparation comprising purified ginsenoside M1 may comprise ginsenoside M1 in an amount of more than 50%, more than 60%, more than 70%, more than 80%, more than 90%, or 100% (w/w) of the total preparation. It should be understood that when a certain number was used herein to show a ratio or dosage, said number generally includes that within the range of 10% more and less, or more specifically, the scope of 5% more and less than the number.

The present invention provides a method for treating lupus nephritis comprising administering a therapeutically effective amount of ginsenoside M1 to a subject in need of such treatment. Also provided is use of ginsenoside M1 for manufacturing a medicament for treating lupus nephritis a subject in need of such treatment. The medicament of the invention is effective in reducing one or more symptoms of lupus nephritis in the subject, selected from the group consisting of (1) in the glomerulus: intrinsic cell proliferation, crescents, neutrophil infiltration and fibrinoid necrosis; and (2) in the tubulointerstitial compartment: interstitial (especially peri-glomerular) mononuclear leukocyte inflammation and tubular atrophy with proteinaceous casts. Also the medicament of the invention is effective in reducing proteinuria or hematuria or lowering serum urea nitrogen level or serum creatinine level in the subject.

The term "individual" or "subject" used herein includes human and non-human animals such as companion animals (such as dogs, cats and the like), farm animals (such as cows, sheep, pigs, horses and the like), or laboratory animals (such as rats, mice, guinea pigs and the like).

The term "treating" as used herein refers to the application or administration of a composition including one or more active agents to a subject afflicted with a disorder, a symptom or conditions of the disorder, or a progression of the disorder, with the purpose to cure, heal, alleviate, relieve, alter, remedy, ameliorate, improve, or affect the disorder, the symptoms or conditions of the disorder, the disabilities induced by the disorder, or the progression of the disorder.

The term "therapeutically effective amount" used herein refers to the amount of an active ingredient to confer a therapeutic effect in a treated subject. For example, an effective amount for treating lupus nephritis is an amount that can prohibit, improve, alleviate or reduce one or more symptoms or conditions such as (1) in the glomerulus: intrinsic cell proliferation, crescents, neutrophil infiltration and fibrinoid necrosis; or (2) in the tubulointerstitial compartment: interstitial (especially peri-glomerular) mononuclear leukocyte inflammation and tubular atrophy with proteinaceous casts, or proteinuria or hematuria, or abnormally elevated serum urea nitrogen level or serum creatinine level, in a subject having lupus nephritis. The symptoms may be determined and evaluated using methods known in the art based on various disease progress-related indexes, for example by analyzing the amount of urine protein, blood urea nitrogen or serum creatinine, or by analyzing renal sections. The therapeutically effective amount may change depending on various reasons, such as administration route and frequency, body weight and species of the individual receiving said pharmaceutical, and purpose of administration. Persons skilled in the art may determine the dosage in each case based on the disclosure herein, established methods, and their own experience. For example, in certain embodiments, the oral dosage of ginsenoside M1 used in the present invention is 10 to 1,000 mg/kg daily. In some examples, the oral the oral dosage of ginsenoside M1 used in the present invention is 100 to 300 mg/kg daily, 50 to 150 mg/kg daily, 25 to 100 mg/kg daily, 10 to 50 mg/kg daily, or 5 to 30 mg/kg daily. In addition, in some embodiments of the invention, ginsenoside M1 is administered periodically for a certain period of time, for example, daily administration for at least 15 days, one month or two months or longer.

According to the present invention, ginsenoside M1 may be used as an active ingredient for treating lupus nephritis. In one embodiment, a therapeutically effective amount of the active ingredient may be formulated with a pharmaceutically acceptable carrier into a pharmaceutical composition of an appropriate form for the purpose of delivery and absorption. Depending on the mode of administration, the pharmaceutical composition of the present invention preferably comprises about 0.1% by weight to about 100% by weight of the active ingredient, wherein the percentage by weight is calculated based on the weight of the whole composition.

As used herein, "pharmaceutically acceptable" means that the carrier is compatible with the active ingredient in the composition, and preferably can stabilize said active ingredient and is safe to the individual receiving the treatment. Said carrier may be a diluent, vehicle, excipient, or matrix to the active ingredient. Some examples of appropriate excipients include lactose, dextrose, sucrose, sorbose, mannose, starch, Arabic gum, calcium phosphate, alginates, tragacanth gum, gelatin, calcium silicate, microcrystalline cellulose, polyvinyl pyrrolidone, cellulose, sterilized water, syrup, and methylcellulose. The composition may additionally comprise lubricants, such as talc, magnesium stearate, and mineral oil; wetting agents; emulsifying and suspending agents; preservatives, such as methyl and propyl hydroxybenzoates; sweeteners; and flavoring agents. The composition of the present invention can provide the effect of rapid, continued, or delayed release of the active ingredient after administration to the patient.

According to the present invention, the form of said composition may be tablets, pills, powder, lozenges, packets, troches, elixers, suspensions, lotions, solutions, syrups, soft and hard gelatin capsules, suppositories, sterilized injection fluid, and packaged powder.

The composition of the present invention may be delivered via any physiologically acceptable route, such as oral, parenteral (such as intramuscular, intravenous, subcutaneous, and intraperitoneal), transdermal, suppository, and intranasal methods. Regarding parenteral administration, it is preferably used in the form of a sterile water solution, which may comprise other substances, such as salts or glucose sufficient to make the solution isotonic to blood. The water solution may be appropriately buffered (preferably with a pH value of 3 to 9) as needed. Preparation of an appropriate parenteral composition under sterile conditions may be accomplished with standard pharmacological techniques well known to persons skilled in the art, and no extra creative labor is required.

According to the present invention, ginsenoside M1 or compositions comprising ginsenoside M1 as the active ingredient may be used in treating individuals with lupus nephritis. Specifically, ginsenoside M1 or compositions comprising ginsenoside M1 as the active ingredient may be administered to individuals with lupus nephritis or individuals with the risk of acquiring lupus nephritis so as to prevent occurrence of the disease or improve the symptoms or delay deterioration of the symptoms.

In addition, according to the present invention, ginsenoside M1 or compositions comprising ginsenoside M1 as the active ingredient may be used in combination with existing therapeutic methods or medicaments, such as pharmaceutical treatment, including but not limited to corticosteroids (such as prednisolone), non-steriodal anti-inflammatory drugs (NSAIDs), cytotoxic drugs (such as cyclophosphamide, chlorambucil, and azathioprine), immunosuppressants (such as cyclosporine and Mycophenolate Mofetil), and vasodilators (such as angiotensin-converting-enzyme inhibitors (ACE inhibitors)). In one embodiment, the medicament or therapeutic method used in combination may be used simultaneously (parallel) or sequentially. When medicaments are used in combination, the medicaments may be mixed in the same formula or put in different formulas separately, such as separate capsules, pills, tablets, and injections.

The present invention is further illustrated by the following examples, which are provided for the purpose of demonstration rather than limitation.

EXAMPLE

1. Materials and Methods 1.1 Animal Model and Experimental Protocol

Female NZB/W F1 mice were purchased from Jackson Lab. All animal experiments were performed with the ethical approval of the Institutional Animal Care and Use Committee of The National Defense Medical Center, Taiwan and performed according to the ethical rules in NIH Guide for the Care and Use of Laboratory Animals.

An accelerated severe lupus nephritis (ASLN) mouse model was established in 8-week-old female NZB/W F1 mice by twice weekly intraperitoneal injection of lipopolysaccharide (LPS, 20 mg/kg body weight) (Sigma, NO, USA) as described in Shui et al., 2007 [51]. Two days after first dose of LPS for the ASLN induction, the mice were divided into two groups of more than 6 mice each and daily administrated with ginsenoside M1 or vehicle (normal saline) via oral gavage till mice sacrificed. 8-Week-old NZB/W F1 female mice (prior to onset of autoantibody production), injected with normal saline, were used as normal controls. All mice were killed at week 5 after disease induction. The tissue specimens of spleen, renal cortical tissue, blood, and urine were collected at the indicated times and stored appropriately before analysis.

1.2 Ginsenoside M1

Ginsenoside M1, 20-O-β-D-glucopyranosyl-20(S)-protopanaxadiol, was prepared by methods known in the art, such as those described in Taiwan Patent Application No. 094116005 (1280982) and U.S. Pat. No. 7,932,057.

1.3 Analysis of Urine Protein and Renal Function

Urine samples were collected in metabolic cages every week and urine protein levels were measured, and serum samples were collected to measure serum levels of blood urea nitrogen (BUN) and creatinine (Cr) as described previously (Ka, S. M. et al. Decoy receptor 3 ameliorates an autoimmune crescentic glomerulonephritis model in mice. *J Am Soc Nephrol* 18:2473-2485; 2007).

1.4 Pathologic Evaluation

Renal tissues were formalin-fixed, embedded in paraffin, and sections (3 μm) prepared and stained with hematoxylin and eosin (H&E) for renal histopathology as described previously. Quantitative analysis was performed by optical microscopy (Olympus BX51, Reflected Fluorescence System, Japan). The examination of renal pathology and scoring were performed in a blinded manner by a pathologist, and the severity of renal lesions was scored. The percentage of glomeruli showing proliferation, neutrophil infiltration, crescent formation, fibrinoid necrosis, and periglomerular inflammation was calculated from at least 100 randomly sampled glomeruli.

1.5 Measurement of Serum Anti-dsDNA Antibodies

Serum levels of anti-dsDNA antibodies were measured using an anti-mouse dsDNA enzyme-linked immunosorbent assay (ELISA) kit (Alpha Diagnostic, TX, USA) according to the manufacturer's instructions. The absorbance at 450 nm was measured using an ELISA plate reader (Bio-Tek, VT, USA).

1.6 Analysis of T Cell Activation

Splenocytes from the mice were prepared as described previously, then were cultured in triplicate in wells ($2.5 \times 10^5$ cells/well) in 96-well flat-bottom microtiter plates previously coated overnight at 4° C. with 0.25 µg/ml anti-mouse CD3 (145-2C11) antibodies (BD Biosciences). After 48 h, the cultures were pulsed with 1 µl of $^3$H-methyl thymidine (Amersham Pharmacia Biotech, Piscataway, N.J.) and harvested 16-18 h later, and the incorporated $^3$H-methyl thymidine was measured using a Top Count (Packard, PerkinElmer, Boston, Mass.) as described previously.

1.7 Measurement of Reactive Oxygen Species (ROS)

Kidney in situ superoxide anion production was determined by dihydroethidium (DHE) labeling. Fluorescent images were quantified by counting the percentage of positive nuclei in the total nuclei per kidney cross-section. Superoxide anion levels in serum and kidney tissues were measured as described previously and the results expressed as reactive luminescence units (RLU) per 15 min per milligram dry weight (i.e., RLU/15 min/mg dry weight).

1.8 Serum Cytokine Detection

To detect the level of IFN-γ, MCP-1, IL-12 p70, IL-6, TNF-α and IL-10 in serum by using BD Cytometric Bead Array Mouse Inflammation kit (BD Biosciences), according to the standard protocol, followed by flow cytometry (BD Biosciences).

1.9 Real-Time PCR

Renal cortex RNA was extracted using TRIzol reagent (Invitrogen) according to the manufacturer's instructions, and real-time reverse transcription-polymerase chain reaction (RT-PCR) was used to measure Toll-like receptor (TLR)7 gene expression. Real-time quantification was performed using a Bio-Rad iCycler iQ system according to the manufacturer's instructions. Amplifications were normalized to the values for GAPDH using the $2^{-\Delta Ct}$ method.

1.10 Statistical Analysis

The results are presented as the mean±SEM. Comparisons between two groups were performed using Student's t test. A p value of <0.05 was considered statistically significant.

2. Results 2.1 Ginsenoside M1 Ameliorated Lupus Nephritis

Figure 1:
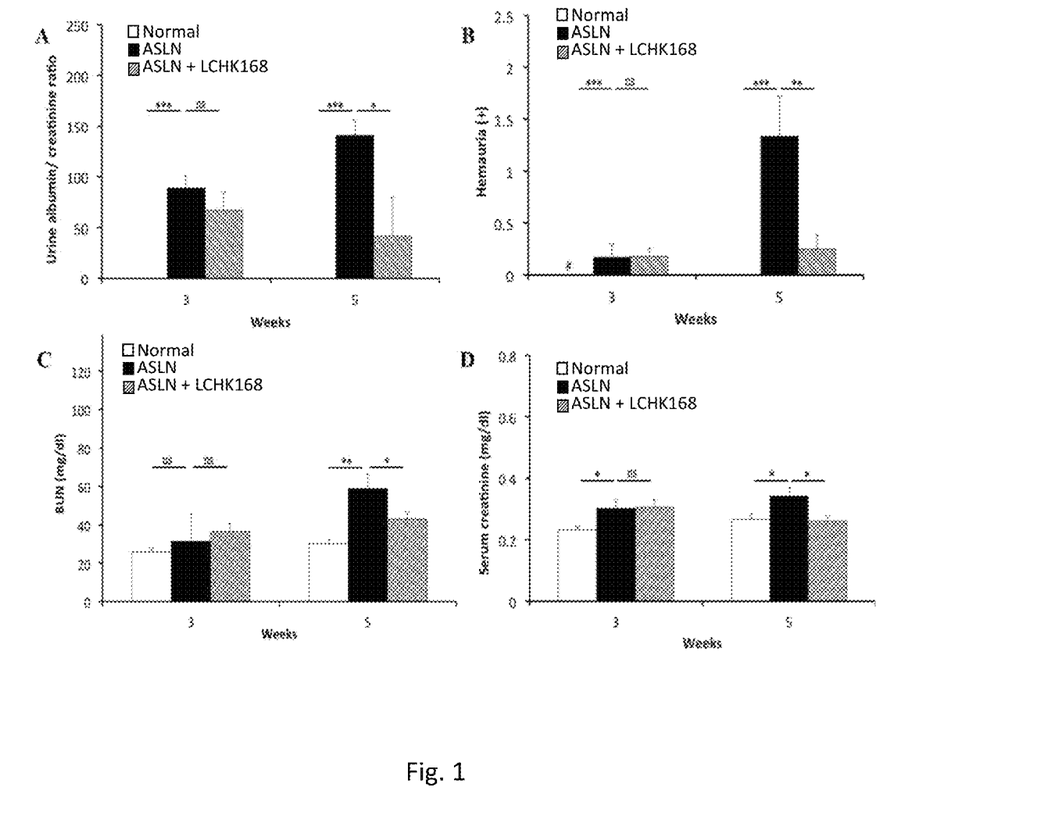
FIG. 1 shows the assessment of urine protein, hematuria and renal function in mice. (A) urine albumin/creatinine ratio, (B) hematuria levels, (C) blood urea nitrogen (BUN) levels, (D) serum creatinine. Each bar represents the mean±SE. *$p<0.05$ and $p<0.01$, and *$p<0.005$. The symbol "#" means "not detectable". The symbol "ns" means "not significant".

To detect proteinuria, compared to normal control group of mice, ASLN group of mice showed significantly increased proteinuria (FIG. 1A) and hematuria (FIG. 1B) (p<0.005). Compared with ASLN group of mice, the magnitudes of proteinuria and hematuria were significantly decreased in the ASLN+LCHK168 group of mice To detect the protection of renal function in mice treated with LCHK168, compared to normal control group of mice, ASLN group of mice showed significantly increased BUN (FIG. 1C) and serum creatinine (FIG. 1D) (p<0.05). Compared with ASLN group of mice, the serum levels of BUN and creatinine were significantly decreased in the ASLN+LCHK168 group of mice (p<0.05).

Figure 2:
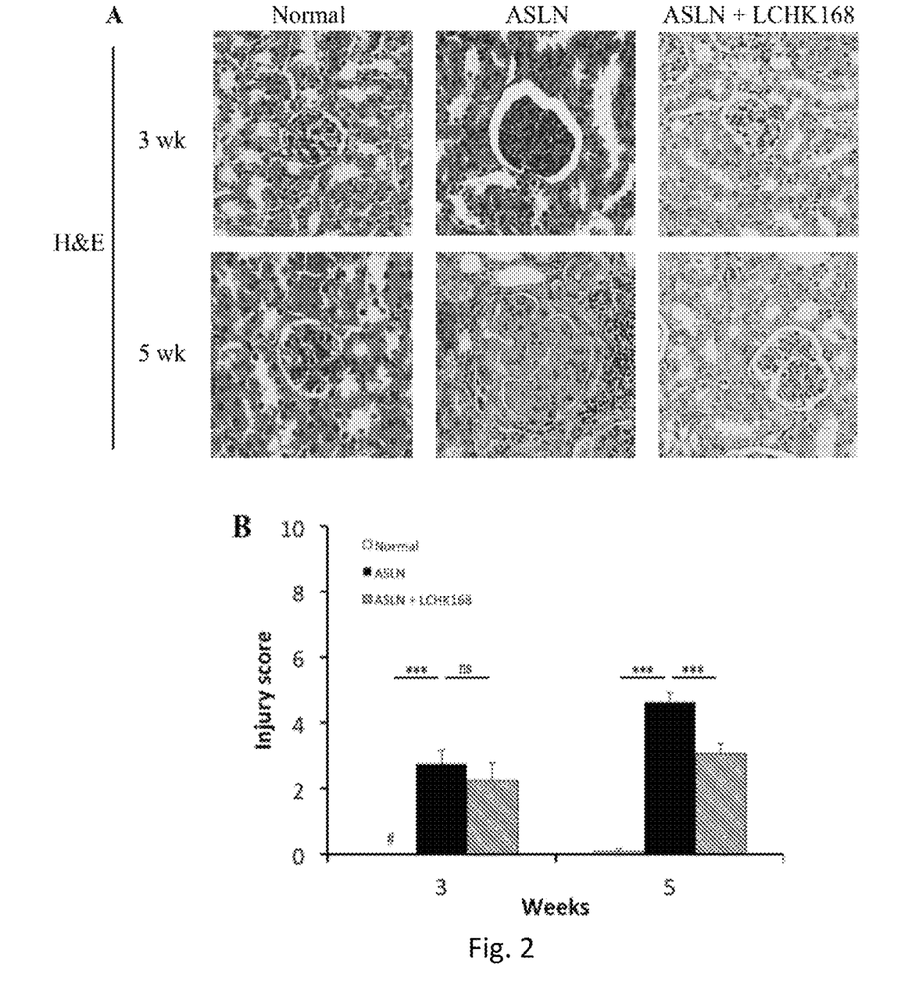
FIG. 2 shows the (A) renal histopathological evaluation by H&E staining (original magnification, ×400 each), and (B) scoring (semi-quantitative analysis). Each bar represents the mean±SE. ***$p<0.005$ represent statistical significance. The symbol "#" means "not detectable". The symbol "ns" means "not significant".

In addition, light microscopy showed severe renal lesions, including neutrocyte infiltration, glomerular crescent-like formation, and tubulointerstitial (especially periglomerular) inflammation, tubular atrophy and proteinaceous casts and fibrinoid necrosis, in the disease-control ASLN mice treated with vehicle (ASLN+vehicle mice) (FIG. 2). In contrast, such renal lesions were greatly decreased in ASLN+M1 mice (all p<0.005) (FIG. 2), although mild glomerular proliferation was present.

2.2 Measurement of Serum Autoantibody Level

Figure 3:
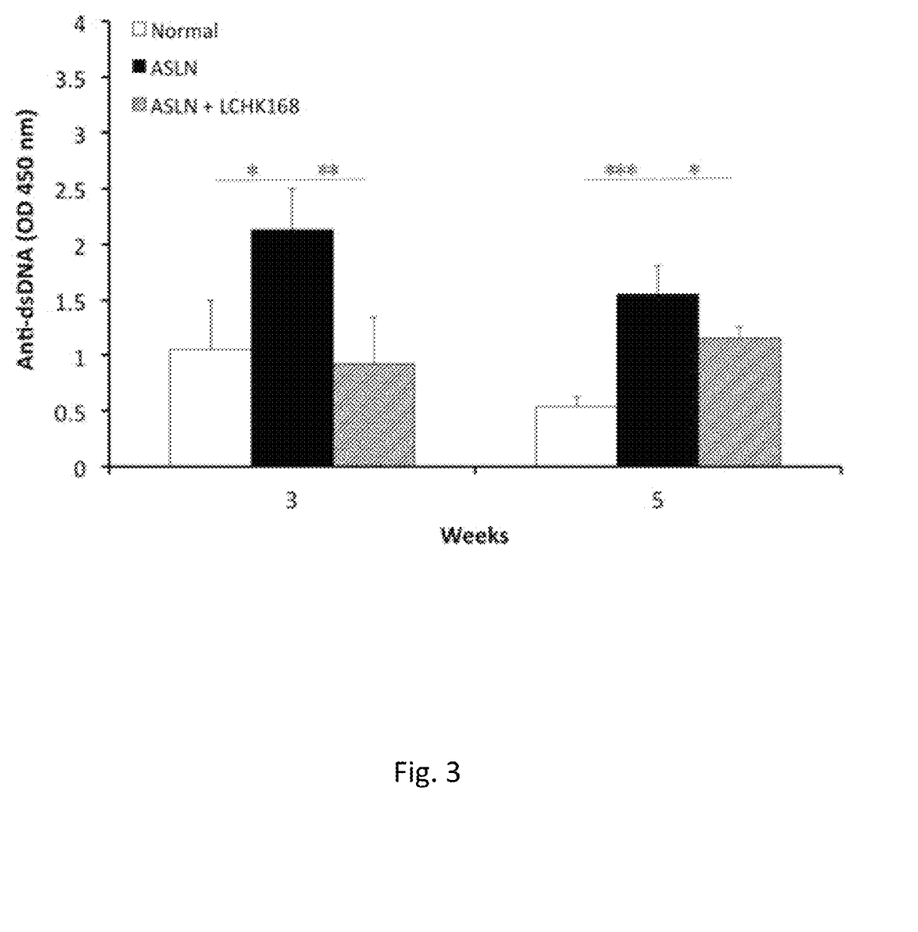
FIG. 3 shows the serum anti-dsDNA antibody levels in mice. Each bar represents the mean±SE. *$p<0.05$, *$p<0.01$, **$p<0.005$.

Since autoantibody-induced immune complex deposition in the kidneys is considered to be the primary cause of lupus nephritis, we measured anti-dsDNA autoantibody levels in the serum. As shown in FIG. 3, serum anti-dsDNA antibody levels were significantly higher in the ASLN group of mice than normal control mice. Then, compared with ASLN group of mice, the serum levels of dsDNA was significantly decreased in the ASLN+LCHK168 group of mice (p<0.01).

2.3 Ginsenoside M1 Reduced Renal ROS Production

Figure 4:
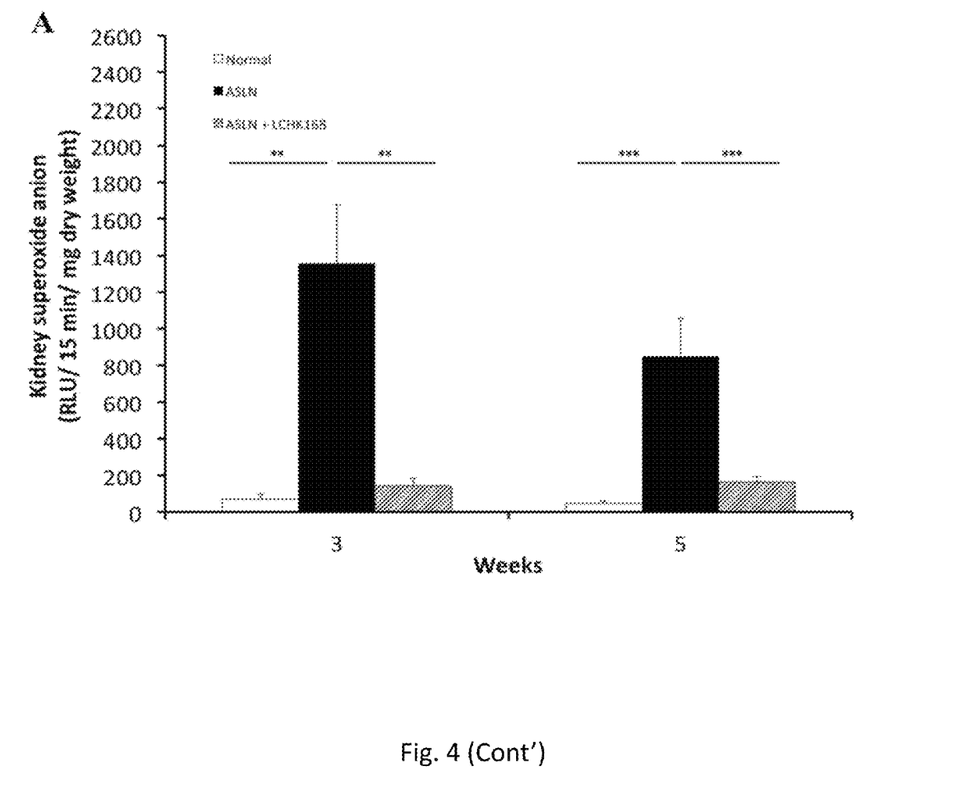
FIG. 4 shows the (A) superoxide anion levels in renal tissues of mice, (B) renal in situ ROS production (original magnification is ×400 each), and (C) semi-quantitative analysis of % of positive-stained nuclei. Each bar represents the mean±SE. $p<0.01$, **$p<0.005$.

Compared to normal control mice, ASLN group of mice showed significantly increased the expression renal ROS production as early as week 3 and dramatically increased at week 5 in ASLN group of mice. Compared with ASLN group of mice, the expression of renal ROS production was significantly decreased in the ASLN+LCHK168 group of mice (p<0.01) (FIG. 4A).

To more specifically detect local ROS production in the kidney, an in situ detection of ROS production in renal tissue was performed, using the DHE assay. As shown in FIGS. 4B and 4C, although DHE fluorescence was low in the normal mouse kidneys, it was significantly increased in the kidneys of ASLN control mice at week 3, and even further enhanced at week 5, thus indicating that in situ ROS production was increased in ASLN group of mice compared to normal control mice. In contrast, very low DHE fluorescence intensity was seen in the ASLN+LCHK168 treatment group, at both week 3 and week 5.

2.4 Suppression of Serum Inflammatory Cytokine Expression with LCHK168.

Figure 5:
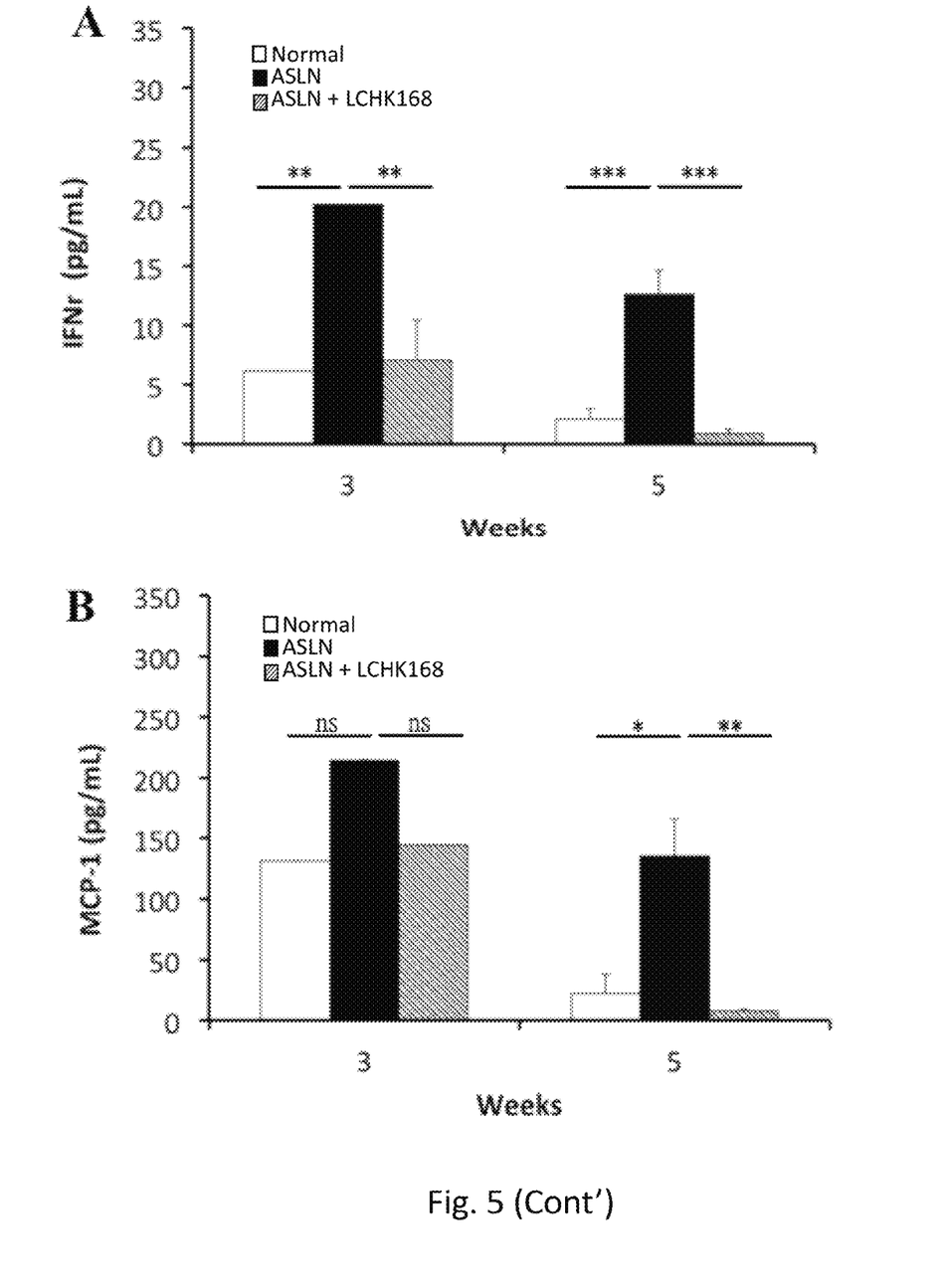
FIG. 5 shows the serum levels of inflammatory cytokines. (A) IFN-γ, (B) MCP-1, (C) IL-12 p70, (D) IL-6, (E) TNF-α and (F) IL-10. Each bar represents the mean±SE. *$p<0.05$, $p<0.01$, *$p<0.005$. The symbol "#" means "not detectable". The symbol "ns" means "not significant".

To measure the serum levels of interferon-γ (IFN-γ), monocyte chemotactic protein 1 (MCP-1), IL-12 p70, IL-6, TNFα, and IL-10 in the mice. As shown in FIG. 5A, serum levels of IFN-γ were significantly increased as early as week 3 and dramatically increased at week 5 in ASLN group of mice. Compared with ASLN group of mice, the expression of IFN-γ was significant decreased in the ASLN+LCHK168 group of mice (p<0.01). Then, as shown in FIG. 5B-F, serum levels of MCP-1, IL-12 p70, IL-6, TNFα, and IL-10 were significantly increased as early as week 3 and dramatically increased at week 5 in ASLN group of mice. Compared with ASLN group of mice, the expression of MCP-1, IL-12 p70, IL-6, TNFα, and IL-10 was significantly decreased in the ASLN+LCHK168 group of mice (p<0.005).

2.5 Ginsenoside M1 Inhibited Proliferation of T Cells

Figure 6:
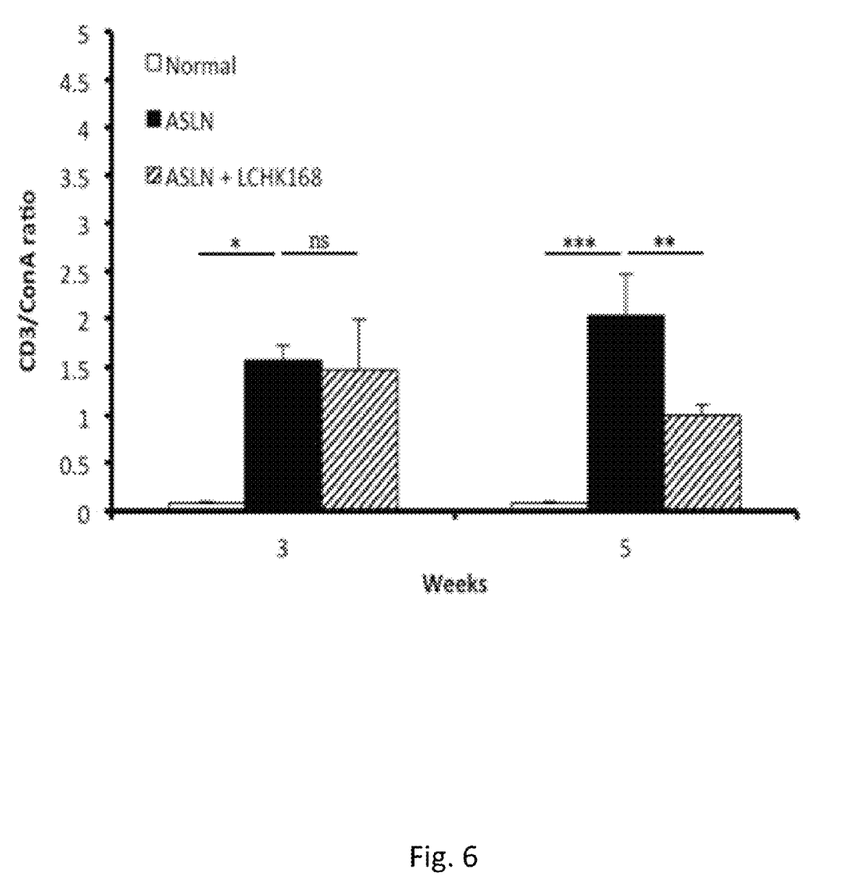
FIG. 6 shows the T cell proliferation in splenocytes of mice. Each bar represents the mean±SE. *$p<0.05$, $p<0.01$, *$p<0.005$. The symbol "ns" means "not significant".

Compared to normal control mice, ASLN group of mice showed significantly increased proliferation of T cells in splenocytes as early as week 3 and dramatically increased at week 5 in ASLN group of mice. Compared with ASLN group of mice, the proliferation of T cells in splenocytes was significant decreased in the ASLN+LCHK168 group of mice (p<0.01) (FIG. 6)

2.6 Inhibition of Toll-Like Receptor 7 mRNA Production.

Figure 7:
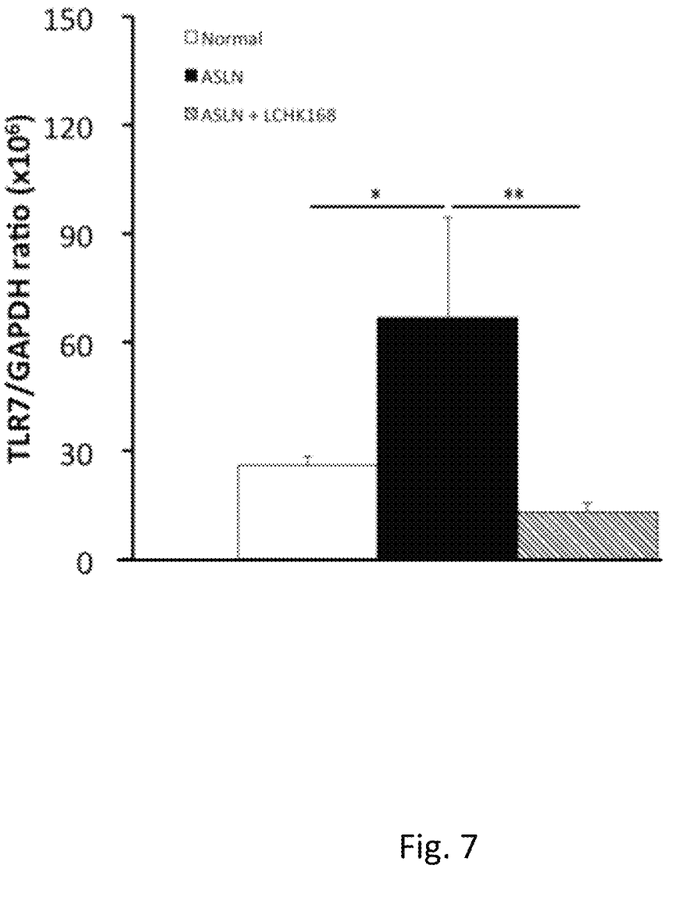
FIG. 7 shows the mRNA levels of TLR7. Each bar represents the mean±SE. *$p<0.05$, **$p<0.01$.

Results of real-time RT-PCR demonstrated increased renal TLR7 mRNA levels, as shown in FIG. 7, mRNA levels of TLR7 were significantly increased in ASLN group of mice (p<0.005). Compared with ASLN group of mice, the mRNA levels of TLR7 was significantly decreased in the ASLN+LCHK168 group of mice (p<0.01).

In summary, our study shows that ginsenoside M1 is effective in preventing development of lupus nephritis. All these findings suggest that ginsenoside M can be further developed to a candidate new drug for the treatment of lupus nephritis.

It is believed that a person of ordinary knowledge in the art where the present invention belongs can utilize the present invention to its broadest scope based on the descriptions herein with no need of further illustration. Therefore, the descriptions and claims as provided should be understood as of demonstrative purpose instead of limitative in any way to the scope of the present invention.

We claim:

1. A method of treating lupus nephritis comprising administering a therapeutically effective amount of ginsenoside M1 to a subject in need.

2. The method of claim 1, wherein the method is effective in reducing or alleviating one or more symptoms of lupus nephritis selected from the group consisting of (1) in the glomerulus: intrinsic cell proliferation, crescents, neutrophil infiltration and fibrinoid necrosis; and (2) in the tubulointerstitial compartment: interstitial mononuclear leukocyte inflammation and tubular atrophy with proteinaceous casts, in the subject.

3. The method of claim 1, wherein the method is effective in reducing peri-glomerular mononuclear leukocyte inflammation in the subject.

4. The method of claim 1, wherein the method is effective in reducing proteinuria or hematuria or lowering serum urea nitrogen level or serum creatinine level in the subject.

5. The method of claim 1, wherein the ginsenoside M1 is administered in combination with one or more therapeutic agents for treating lupus nephritis, selected from the group consisting of corticosteroids, non-steriodal anti-inflammatory drugs (NSAIDs), cytotoxic drugs, immunosuppressants, and vasodilators.

* * * * *